United States Patent [19]

Kim et al.

[11] Patent Number: 5,567,813
[45] Date of Patent: Oct. 22, 1996

[54] PROCESS FOR PREPARING CEPHALOSPORIN COMPOUNDS FROM REACTIVE ORGANIC ACID DERIVATIVES

[75] Inventors: Sung K. Kim; Jong C. Lim; Seong N. Kim, all of Youseong-ku; Hee M. Oh; Woo H. Kim, both of Seo-ku, all of Rep. of Korea

[73] Assignee: Lucky Ltd., Seoul, Rep. of Korea

[21] Appl. No.: 258,184

[22] Filed: Jun. 10, 1994

[30] Foreign Application Priority Data

Jun. 10, 1993 [KR] Rep. of Korea .................. 93-10542
Mar. 21, 1994 [KR] Rep. of Korea .................. 94-5658

[51] Int. Cl.$^6$ ........................................... C07D 501/06
[52] U.S. Cl. .................. 540/222; 540/223; 540/225; 540/227; 540/228
[58] Field of Search ........................... 540/222, 225, 540/215, 223, 227, 228

[56] References Cited

U.S. PATENT DOCUMENTS 4,098,888  7/1978  Ochiai et al. .................. 424/246
5,317,099  5/1996  Lee et al. .................. 540/222

*Primary Examiner*—John M. Ford
*Attorney, Agent, or Firm*—Birch, Stewart, Kolasch & Birch, LLP

[57] ABSTRACT

The present invention provides a process for preparing cephem derivatives having the following general formula (I):

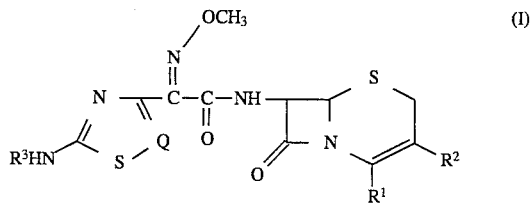

in which $R^1$ represents a carboxy group or a protected carboxy group which can form the salt of —COO⁻M⁺ with an alkali metal ion (M⁺) such as sodium, or may represent —COO⁻ when $R^2$ has a substituent having positive electric charge such as pyridinium, pyrimidinium or thiazolium, $R^2$ represents hydrogen, acyloxymethyl, heterocyclic methyl or heterocyclic thiomethyl, each of which can be substituted with appropriate substituents, $R^3$ represents hydrogen or an amino-protecting group, $R^4$ represents $C_1$–$C_4$ alkyl or phenyl, or together with the oxygen or phosphorus atom to which it is attached may form a 5- or 6-membered heterocyclic ring, and Q represents N or CH, characterized in that a reactive thiophosphate derivative of thia(dia)zole acetic acid having the following general formula (II):

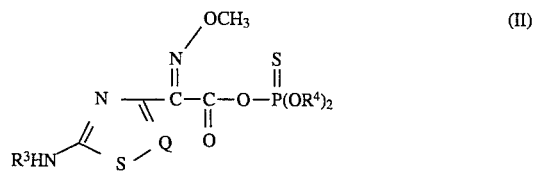

wherein $R^3$, $R^4$ and Q are defined as above is acylated with an 7-ACA derivative having the following general formula (III):

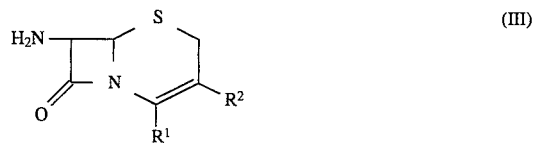

wherein $R^1$ and $R^2$ are defined as above, in the presence of a solvent and a base.

12 Claims, No Drawings

PROCESS FOR PREPARING CEPHALOSPORIN COMPOUNDS FROM REACTIVE ORGANIC ACID DERIVATIVES

BACKGROUND OR THE INVENTION

1. Field of the Invention

The present invention relates to a novel process for preparing cephalosporin compounds useful as antibiotics. More specifically, the present invention relates to a novel process for preparing cephem derivatives represented by the following formula (I) having 2-[aminothia(dia)zolyl]-2-methoxyiminoacetamido group on the 7-position of cephem nucleus, characterized in that a reactive thiophosphate of thia(dia)zole acetic acid having the following formula (II) (hereinafter referred as to "the reactive organic acid derivative") is acylated with a 7-ACA (7-aminocephalosporanic acid) derivative:

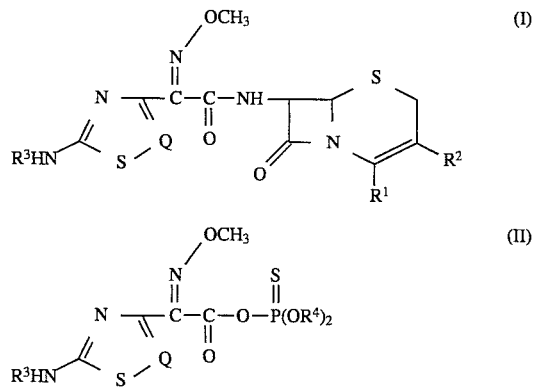

in which $R^1$ represents a carboxy group or a protected carboxy group which can form the salt of —COO$^-$M$^+$ with an alkali metal ion (M$^+$) such as sodium, or may represent —COO$^-$ when $R^2$ has a substituent having positive electric charge such as pyridinium, pyrimidinium or thiazolium, $R^2$ represents hydrogen, acyloxymethyl, heterocyclic methyl or heterocyclic thiomethyl, each of which can be substituted with appropriate substituents, $R^3$ represents hydrogen or an amino-protecting group, $R^4$ represents $C_1$–$C_4$ alkyl or phenyl, or together with the oxygen or phosphorus atom to which it is attached may form a 5- or 6-membered heterocyclic ring, and Q represents N or CH.

2. Background Art

In general, numerous methods for preparing β-lactam antibiotics have been disclosed in prior publications and patent specifications. Such prior methods prepare the β-lactam antibiotic compounds commonly starting from an organic acid represented by the following formula (A) which is converted into a reactive derivative thereof and then subjected to the acylation reaction with an amino group of the β-lactam nucleus:

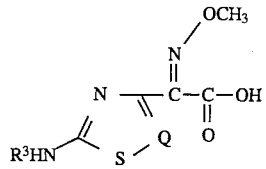

wherein $R^3$ and Q are defined as previously described.

The reactive derivatives which have been known from the above prior methods include an acid chloride, a reactive ester, a reactive amide, a mixed acid anhydride and the like. However, the reactive derivative in the form of an acid chloride or a mixed acid anhydride is prepared under a stringent reaction condition and further is unstable so that it might be used in situ for the acylation reaction without isolation. This may be the major reason for the formation of by-products. In addition, the reactive ester and the reactive amide have also disadvantages in that they are prepared in a low yield, their reactivity is very low and so requires long reaction time, and further the reaction by-products, for example, a hydroxy derivative such as 1-hydroxybenzotriazole and a thiol derivative such as 2-mercaptobenzothiazole can be hardly removed.

Thus, the present inventors have continuously studied to find out a method which can solve the problems involved in the known reactive derivatives as previously described and succeeded in preparing a novel reactive derivative having a suitable reactivity and stability in a high yield and a high purity from the organic acid of formula (A) and a chlorothiophosphate derivative by means of a convenient method (see U.S. patent application Ser. No. 08/223,756, filed Apr. 6, 1995). Further, now we have disclosed that the cephem derivative of formula (I) useful as an antibiotic can be more economically prepared starting from said reactive organic acid derivative and then completed the present invention.

Therefore, it is an object of the present invention to provide a novel process for preparing cephem derivatives represented by the formula (I) as defined above.

It is a further object of the present invention to provide a novel process for preparing cephem derivatives, as defined above, starting from a reactive thiophosphate derivative of thia(dia)zole acetic acid having the formula (II) as defined above.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a novel process for preapring cephem derivatives represented by the following formula (I), characterized in that a reactive thiophosphate derivative of thia(dia)zole acetic acid of formula (II) is acylated with an 7-ACA derivative of formula (III) in the presence of a solvent and a base according to the following reaction scheme:

Reaction Scheme

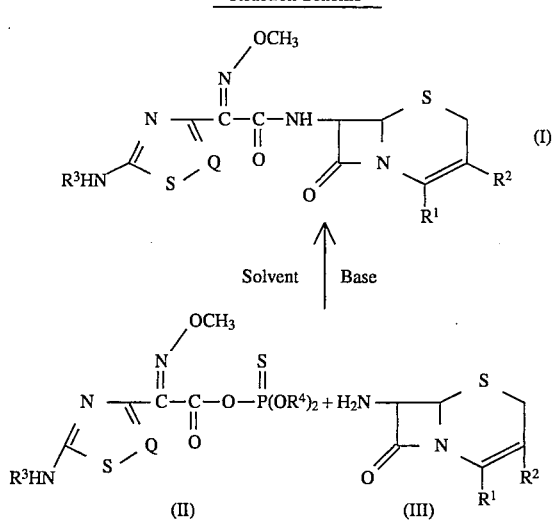

In the above reaction scheme, $R^1$ represents a carboxy group or a protected carboxy group which can form the salt of —COO⁻M⁺ with an alkali metal ion (M⁺) such as sodium, or may represent —COO⁻ when $R^2$ has a substituent having positive electric charge such as pyridinium, pyrimidinium or thiazolium, $R^2$ represents hydrogen, acyloxymethyl, heterocyclic methyl or heterocyclic thiomethyl, each of which can be substituted with appropriate substituents, $R^3$ represents hydrogen or an amino-protecting group, $R^4$ represents $C_1$–$C_4$ alkyl or phenyl, or together with the oxygen or phosphorus atom to which it is attached may form a 5- or 6-membered heterocyclic ring, and Q represents N or CH.

In the term "acyloxymethyl" used in the specification of the present invention, the definition of "acyl" includes any acyl group conventionally known in the beta-lactam field such as carbamoyl, aliphatic acyl groups, acyl groups having an aromatic or heterocyclic ring, etc. Preferred example of the acyl group may include $C_1$–$C_4$ alkanoyl such as formyl, acetyl, propionyl, butyryl, etc., particularly $C_1$–$C_2$ alkanoyl.

In the terms "heterocyclic methyl" and "heterocyclic thiomethyl", the definition of "heterocyclic" may include a saturated or unsaturated 3- to 7-membered monocycle containing at least one heteroatom selected from nitrogen, oxygen and sulfur atoms in the ring or a polycycle which is formed by fusion of two or more monocycles as defined above. Typical example of said heterocycle is pyrrolidinyl, imidazolinyl, piperidino, piperazinyl, morpholinyl, thiazolidinyl, pyrrolyl, pyrrolinyl, imidazolyl, pyrazolyl, pyridyl, pyrimidinyl, pyrazinyl, pyridazinyl, triazolyl (for example, 4H-1,2,4-triazolyl, etc.), oxazolyl, isoxazolyl, oxadiazolyl (for example, 1,2,4-oxadiazolyl, etc.), thiazolyl, thiazolinyl, thiadiazolyl (for example, 1,2,4-thiadiazolyl), thienyl, indolyl, isoindolyl, indolinyl, indolizinyl, benzotriazolyl, tetrazolopyridyl, quinolyl, isoquinolyl, benzoxazolyl, benzothiazolyl, etc., which can have a positive electric charge in the ring, if possible, as in pyridinium, pyrimidinium, thiazolium, etc., and can be substituted with 1 to 4 suitable substituents. In this case, the preferable example of the suitable substituents may include $C_1$–$C_4$ alkyl (for example, methyl, ethyl, propyl, isopropyl, t-butyl, etc.), $C_2$–$C_4$ alkenyl (for example, ethenyl, 1-propenyl, allyl, 1,3-butadienyl, etc.), $C_2$–$C_4$ alkynyl (for example, ethynyl, 1- or 2-propynyl, etc.), $C_3$–$C_6$ cycloalkyl (for example, cyclopropyl, cyclopentyl, etc.), halogen (for example, chlorine, fluorine, iodine, etc.), substituted or unsubstituted amino (for example, amino, methylamino, ethylamino, N,N-dimethylamino, N,N-diethylamino, etc.), phenyl which is substituted or unsubstituted with hydroxy, etc.

The process according to the present invention is characterized by the use of the compound of formula (II) having a suitable reactivity and stability as the reactive organic acid derivative, and therefore, can broadly be applied to the synthesis of the presently known cephalosporin compounds having 2-[aminothia(dia)zolyl]-2-methoxyiminoacetamido group on the 7-position of a cephem nucleus.

In the reaction of the process according to the present invention, the reactive organic acid derivative of formula (II) is advantageously used in a slightly excessive amount with respect to the compound of formula (III) for the completion of the reaction. Generally, the reactive organic acid derivative of formula (II) can be used in an amount of 1.0 to 1.5 equivalent weights with respect to the compound of formula (III). However, in view of the completion of the reaction and economy, the reactive organic acid derivative of formula (II) is preferably used in an amount of 1.0 to 1.2 equivalent weights with respect to the compound of formula (III).

As the base in the reaction of the present invention, both of an inorganic acid and an organic acid can be preferably used. For this purpose, the inorganic base which can be used may include carbonates and bicarbonates of an alkali earth metal such as sodium hydrogen carbonate, sodium carbonate, potassium hydrogen carbonate, potassium carbonate, etc. As the organic base, a tertiary amine such as triethylamine, tri-n-butylamine, diisopropyietnylamine, pyridine, N,N-dimethylaniline, etc. can be used. Among those bases, sodium hydrogen carbonate, triethylamine, tri-n-butylamine and the like can me most preferably used.

Although the used amount of the base can be varied depending on the kind of the substituent $R^2$, the base is used generally in an amount of 1.5 to 3.5 equivalent weight, preferably 2.0 to 3.0 equivalent weight, with respect to the compound of formula (III).

As the solvent in the reaction of the present invention, any polar or non-polar solvent such as dichloromethane, dichloroethane, chloroform, carbon tetrachloride, toluene, xylene, acetonitrile, ethyl acetate, dioxane, tetrahydrofuran, acetone, N,N-dimethylformamide, N,N-dimethylacetamide, alcohols such as methyl alcohol, ethyl alcohol, isopropyl alcohol, water, etc. can be individually used. Particularly, one of the alcohols as mentioned above can be effectively used. However, a mixed solvent of two or more selected from the above-mentioned solvents, for example a mixture of alcohol-water, tetrahydrofuran-water, N,N-dimethylacetamide-dichloromethane, etc., can also be effectively used in order to optimize the reactivity and the separation of the reaction product.

Although the used amount of the solvent used is not critical, the solvent is generally used in an amount of 8 to 50 ml, preferably of 10 to 30 ml, with respect to 10 mmol of the starting material.

The reaction temperature in the present invention should not be restricted unless the selected temperature adversely affects the reaction of the present invention. However, the reaction can generally be completed within 2 to 6 hours at a temperature of 0° to 30° C., particularly even in the range of room temperature of 20° to 25° C. to readily prepare the desired compound.

In the above reaction scheme, when $R^3$ represents an amino-protecting group, if desired, the acyl compound resulting from the reaction can be subjected to a deprotecting reaction to remove the protecting group to obtain the desired compound of formula (I) wherein $R^3$ represents hydrogen.

The reactive organic acid derivative of formula (II) which is used as the starting compound in the present invention can readily be prepared according to the method disclosed in Korean Patent Application No. 93-6008 as previously described. The compound (II) has a unique physico-chemical property and therefore has a good solubility in a polar or non-polar organic solvent. Further, the compound (II) has a superior stability so that when it is in the state of a solution in said solvent it cannot be decomposed into the organic acid even by washing with an acidic, basic or neutral water. In addition, when the reactive organic acid derivative of formula (II) is used in the acylation reaction with the amino group of β-lactam nucleus, this reaction can be readily practiced even under mild conditions and the thiophosphate derivative produced as a by-product is present in the aqueous layer in a dissolved state and therefore can be readily removed.

In addition, in the reaction according to the present invention, although the compound of formula (II) can be sujected to the acylation reaction after the group $R^3$ is protected with an amino-protecting group, the acylation reaction can also be practiced with the compound of formula (II) having no amino-protecting group without any restriction. Accordingly, when the process according to the present invention is applied to the preparation of the compound of formula (I) industrial scale, there is a great advantage that the final β-lactam antibiotics can readily be synthesized in a high yield and a high purity.

Typical example of the compound which can be prepared according to the process of the present invention may include the following:

3-acetoxymethyl-7-[2-(2-amino-4-thiazolyl) -2-methoxyimino]acetamide-3-cephem-4 -carboxylic acid (Cefotaxime); 7-[[2-(2-amino-4 -thiazolyl)-2-(Z)-methoxyimino]acetamido]-3-[(2,5-dihydro-6-hydroxy -2-methyl-5-oxo-1,2,4-triazin-3-yl) thiomethyl]-3-cephem-4-carboxylic acid (Ceftriaxone); 7-[[α-(2-amino-4-thiazolyl)-2-(Z)-methoxyimino]acetamido]-3-[(1-methyl-1H-tetrazol-5-yl)-thiomethyl]-cephem-4-carboxylic acid (Cefmenoxime); 7-[2-methoxyimino-2-(2-amino -1,3-thiazol-4-yl)acetamido]-3-cephem-4- carboxylic acid (Ceftizoxime); 7-[[2-(2-amino-4-thiazolyl)-2-(Z)-methoxyimino]acetamido] -3-(2,3-dicyclopentenopyridiniummethyl)-3-cephera-4-carboxylate (Cefpirome); 7-[[2-(2-amino-4-thiazolyl)-2-methoxyimino]acetamido]-3-(1-methylpyrrolidiummethyl)-3-cephem-4-carboxylate (Cefepime); 7-[[(Z)-2-(2-amino-4-thiazolyl)-2-methoxyimino]acetamido]-3-(4,6-diamino-1-methylpyrimidinium-2-yl)thiomethyl-3-cephem-4-carboxylate; 7-[ [(Z)-2-(2-amino-1,2,4-thiazol-3-yl)-2-methoxyimino] acetamido]-3-(4,6-diamino-1-methylpyrimidinium-2-yl)thiomethyl -3-cephem-4-carboxylate; 7-[[(Z) -2-(2-amino-1,2,4-thiazol-3-yl) -2-methoxyimino] acetamido]-3-(4,6-diamino-1-ethylpyrimidinium-2-yl) thiomethyl-3-cephem-4-carboxylate; 7-[[(Z) -2-(2- amino-4-thiazolyl) -2-methoxyimino]acetamido]-3-(1, 4,6-triaminopyrimidinium -2-yl) thiomethyl-3-cephem-4-carboxylate; 7-[[(Z)-2-(2-amino-4-thiazolyl) -2-methoxyimino]acetamido]-3-(4,6-diamino-1,5-dimethylpyrimidinium-2-yl)thiomethyl -3-cephem-4-carboxylate; 7-[[(Z)-2-(2-amino -4-thiazolyl) -2-methoxyimino]acetamido] -3-(2,6-diamino-1 -methylpyrimidinium-4-yl)thiomethyl-3-cephem-4-carboxylate; 7-[[(Z)-2-(2-amino-4-thiazolyl)-2-methoxyimino]acetamido]-3- (2,6-diamino -1-ethylpyrimidinium-4-yl)thiomethyl-3-cephem-4-carboxylate; 7-[[(Z) -2-(2-amino-4-thiazolyl) -2-methoxyimino]acetamido]-3-(2,6 -diamino-3-ethylpyrimidinium-4-yl) thiomethyl-3-cephem-4-carboxylate; 7-[[(Z) -2-(2-amino-4-thiazolyl)-2-methoxyimino]-acetamido] -3-(2,6-diamino-3-methylpyrimidinium-4-yl)thiomethyl-3-cephem-4-carboxylate; 7-[[(Z) -2-(2-amino-4-thiazolyl)-2-methoxyimino]acetamido] -3-(4,5,6-triamino-1-methylpyrimidinium-2-yl)thiomethyl-3 -cephem-4-carboxylate; 7-[[(Z) -2-(2-amino-4-thiazolyl)-2-methoxyimino] acetamido]-3-(4-amino-1-methylpyrimidinium-2-yl)thiomethyl-3 -cephem-4-carboxylate; 7-[[(Z)-2-(2-amino-4-thiazolyl)-2-methoxyimino] acetamido]-3-(4-amino-1-methylpyrimidinium-2-yl)-thiomethyl -3-cephem-4-carboxylate; 7-[[(Z) -2-(2-amino-4-thiazolyl)-2-methoxyimino]acetamido]-3-(4-amino-1-carboxymethylpyrimidinium-2-yl) -thiomethyl-3-cephem-4-carboxylate; 7-[[(Z)-2-(2-amino-4-thiazolyl) -2-methoxyimino]acetamido]-3-(4-amino-1-aminopyrimidinium-2 -yl)-thiomethyl-3-cephem-4-carboxylate; 7-[[(Z)-2-(2-amino-4-thiazolyl) -2-methoxyimino]acetamido]-3-(1,4,5-triaminopyrimidinium-2 -yl) thiomethyl-3-cephem-4-carboxylate; 7-[ [(Z)-2-(2-amino-4-thiazolyl) -2-methoxyimino]acetamido]-3-(4-amino-1-meth-yl-6-(N,N-dimethyl) aminopyrimidinium-2-yl)thiomethyl-3-cephem-4-carboxylate; 7-[[(Z)-2-(2-amino-4-thiazolyl)-2-methoxyimino]acet-amido]-3-(1, 4,5,6-tetraaminopyrimidinium-2-yl)thiomethyl-3-cephem-4-carboxylate; 7-[ [(Z)-2-(2-amino-4-thiazolyl)-2-methoxyimino] acetamido] -3-(1,4-diamino-5-methylpyrimidinium-2-yl)thiomethyl-3-cephem-4-carboxylate; 7-[[(Z) -2-(2-amino-4-thiazolyl)-2-methoxyimino]acetamido]-3-(1, 4-diamino-5-ethylpyrimidinium-2-yl)thiomethyl-3-cephem -4-carboxylate; 7-[[(Z)-2-(2-amino-4-thiazolyl)-2-methoxyimino]acetamido]-3-(1,4-diamino-6-(N-methyl)aminopyrimidinium-2-yl) -thiomethyl-3-cephem-4-carboxylate; 7-[[(Z)-2-(2-amino-4-thiazolyl) -2-methox-yimino]acetamido]-3-(1,4-diamino-5-methyl-6-(N-methyl) aminopyrimidinium-2-yl)thiomethyl-3-cephem-4-carbox-ylate; 7-[[(Z)-2-(2-amino-4-thiazolyl)-2-methoxyimino]acetamido]-3-(3,4 -diamino-3,5,6,7-tetrahydrocyclopentapyrimidinium-2-yl)thiomethyl -3-cephem-4-carboxylate; 7-[[(Z)-2-(2-amino-4-thiazolyl)-2-methoxyimino]acetamido]-3-(2-amino-1-methyl-1,5,6, 7-tetrahydrocyclopentapyrimidinium -4-yl)thiomethyl-3-cephem-4-carboxylate; 7-[[(Z)-2 -(2-amino-4-thiazolyl)-2-methoxyimino]acetamido]-3-(1,2-diamino -1,5,6,7-tetrahydrocyclopentapyrimidinium-4-yl) thiomethyl-3-cephem -4-carboxylate; 7-[[(Z)-2-(2-amino-4-thiazolyl)-2-methoxyimino acetamido]-3-(7-amino-1-methyl[1,2,49 triazolo[1,5-c]pyrimidinium -5-yl)thiomethyl-3-cephem-4-carboxylate; or 7-[[(Z)-2-(2-amino -4-thiazolyl)-2-methoxyimino]acetamido]-3-(1-methyl[1,3]imidazo [1,2-c]pyrimidinium-5-yl)thiomethyl-3-cephem-4-carboxylate.

Hereinafter, the present invention will be more specifically explained on the basis of the following examples. However, since the major characteristic feature of the present invention resides in the use of the reactive organic acid derivative of formula (II) in preparing the desired compound as previously described, the technical scope of the present invention should not be limited to the following examples unless such characteristic constitution of the present invention is altered.

PREPARATION EXAMPLE

Synthesis of diethylthiophosphoryl (Z)-(2-aminothiazol-4-yl)methoxyiminoacetate (Z)-(2-aminothiazol-4-yl)methoxyiminoacetic acid (20.1 g), tri-n-butylamine (24.10 g) and 1,4-diazabicyclo[2,2,2 [octane (0.11 g) were suspended in dry dichloromethane (200 ml), and then diethylchlorothiophosphate (24.52 g) was added thereto over 20 minutes while maintaining the solution under nitrogen atmosphere at 0° C. to 5° C. The mixture was stirred for 2 hours. After the reaction was completed, distilled water (300 ml) was added to the reaction solution and the mixture was stirred for 5 minutes. The organic layer was separated, washed successively with 5% aqueous sodium bicarbonate solution (300 ml) and saturated saline (300 ml), dried over magnesium sulfate, filtered and then concentrated under reduced pressure. To the concentrated solution normal hexane (400 ml) was added to solidify the resulting product which was then filtered, washed with normal hexane (100 ml) and dried to obtain 33.2 g (Yield 94.0%) of the title compound as a pale yellow solid.

Melting Point: 87°–88° C.

NMR (δ, CDCl$_3$): 1.38(t, 6H), 4.05(s, 3H), 4.31(m, 4H), 5.49(bs, 2H), 6.87(s, 1H)

EXAMPLE 1

Synthesis of 3-acetoxymethyl-7-[2-(2-amino-4-thiazolyl)-2-methoxyimino]-acetamido-3-cephem-4-carboxylic acid (Cefotaxime)

To distilled water (200 ml) and tetrahydrofuran (200 ml) in a 1 L-round flask were successively added 7-aminocephalosporanic acid (54.46 g), diethylthiophosphoryl-(Z)-(2-aminothiazol-4-yl)methoxyiminoacetate (77.74 g) with stirring. After adding tri-n-butylamine (74.15 g), the reaction mixture was stirred for 3 hours while maintaining the temperature of at 20° to 25° C. and then extracted with 12% aqueous sodium carbonate solution (453 g) and ethyl acetate (100 ml) to remove the organic layer. The separated aqueous layer was extracted again with ethyl acetate (100 ml) to remove the remainder of the organic layer. Then the aqueous layer was neutralized with 20% aqueous sulfuric acid solution to pH 6. To the neutralized aqueous solution was added active carbon (10 g) and then the mixture was stirred for 30 minutes and filtered. The filtrate was saturated with sodium chloride. The saturated aqueous solution was adjusted to pH 4 by adding 20% aqueous sulfuric acid solution. After adding a small amount of the title compound, the mixture was then adjusted to pH 2.5 by further adding 20% aqueous sulfuric acid solution. The crystal was thoroughly precipitated, filtered, washed with water and then dried to obtain 83.8 g (Yield 92%) of the title compound as a pale yellow solid.

HPLC Purity: 98.5[{]jf44a

EXAMPLE 2

Synthesis of 3-acetoxymethyl-7-[2-(2-amino-4-thiazolyl)-2-methoxyimino]-acetamido-3-cephem-4-carboxylic acid (Cefotaxime)

Distilled water (200 ml), 7-aminocephalosporanic acid (54.46 g) and sodium hydrogen carbonate (33.6 g) were introduced into a 1 L round flask and then allowed to completely dissolve by stirring at room temperature. To this reaction solution were added tetrahydrofuran ( 200 ml ) and diethylthiophosphoryl-(Z)-(2-aminothiazol-4-yl)methoxy-iminoacetate (77.74 g) and the mixture was stirred for 5 hours at the temperature of 20° to 25° C. The reaction solution was extracted with ethyl acetate (100 ml) to remove the organic layer and the separated aqueous layer was extracted again with ethyl acetate (100 ml) and then neutralized to pH 6 by adding 20% aqueous sulfuric acid solution. To the neutralized aqueous solution was added active carbon (10 g) and then the mixture was stirred for 30 minutes and filtered. The filtrate was saturated with sodium chloride. This saturated aqueous solution was adjusted to pH 4 by adding 20% aqueous sulfuric acid solution. After adding a small amount of the title compound, the mixture was adjusted again to pH 2.5 by further adding 20% aqueous sulfuric acid solution. After the crystal is thoroughly precipitated, it was filtered, washed with water and then dried to obtain 81.07 g (Yield 89%) of the title compound as a pale yellow solid.

HPLC Purity: 98.6[{]jf44a

EXAMPLE 3

Synthesis of 3-acetoxymethyl-7-[2-(2-amino-4-thiazolyl)-2-methoxyimino]-acetamido-3-cephem-4-carboxylic acid (Cefotaxime)

According to the same procedure as EXAMPLE 2 except that triethylamine (40.48 g) is used instead of sodium hydrogen carbonate, 77.43 g (Yield 85%) of the title compound was obtained.

HPLC Purity: 98.4[{]jf44a

EXAMPLE 4

Synthesis of 3-acetoxymethyl-7-[2-(2-amino-4-thiazolyl)-2-methoxyimino]-acetamido-3-cephem-4-carboxylic acid (Cefotaxime)

According to the same procedure as EXAMPLE 1 except that N,N-dimethylacetamide (100 ml) and dichloromethane (400 ml) are used instead of distilled water and tetrahydrofuran and dichloromethane (100 ml) is used instead of ethyl acetate as an extracting solvent, 82.0 g (Yield 90%) of the title compound was obtained.

HPLC Purity: 98.6[{]jf44a

EXAMPLE 5

Synthesis of 3-acetoxymethyl-7-[2-(2-amino-4-thiazolyl)-2-methoxyimino] -acetamido-3-cephem-4-carboxylic acid (Cefotaxime)

To 95% ethyl alcohol (400 ml) in a 1 L-round flask were successively added 7-aminocephalosporanic acid (54.46 g) and diethylthiophosphoryl-(Z)-(2-aminothiazol-4-yl) methoxyiminoacetate (77.74 g) with stirring. After adding triethylamine (40.48 g), the reaction mixture was stirred for 3 hours while maintaining the temperature of 20° to 25° C. and then concentrated hydrochloric acid (31.25 g) diluted with 95% ethyl alcohol (200 ml) was added thereto. The mixture was vigorously stirred for about one hour to thoroughly precipitate the crystals. The precipitated crystals were filtered, washed with water and then dried to obtain 83.9 g (Yield 92%) of the title compound as a white solid.

HPLC Purity: 98.6[{]jf44a

EXAMPLE 6

Synthesis of 3-acetoxymethyl-7-[2-(2-amino-4-thiazolyl)-2-methoxyimino]-acetamido-3-cephem-4-carboxylic acid (Cefotaxime)

According to the same procedure as EXAMPLE 5 except that distilled water (100 ml) and isopropyl alcohol (400 ml) are used instead of ethyl alcohol, 82.0 g (Yield 90%) of the title compound was obtained.

HPLC Purity: 98.4[{]jf44a

EXAMPLE 7

Synthesis of 7-[[2-(2-amino-4-thiazolyl)-2-(Z)-methoxy-imino] acetamido]-3-[1,2,5-dihydro-6-hydroxy-2-methyl-5- oxo-1,2,4-triazin-3-yl)thiomethyl]-3-cephem-4-carboxylic acid (Ceftriaxone)

To distilled water (200 ml) and tetrahydrofuran (200 ml) in a 1 L-round flask were successively added 7-amino-3-[(2,5-dihydro-6-hydroxy-2-methyl-5-oxo-1,2,4-triazin-3-yl)thiomethyl]-3-cephem-4-carboxylic acid (37.1 g), diethylthiophosphoryl-(Z)-(2-aminothiazol-4-yl)methoxyiminoacetate (38.8 g) and tri-n-butylamine (55.7 g) with stirring. This reaction solution was stirred for 3 hours while maintaining the temperature at 20° to 25° C. and then toluene (200 ml) was added thereto to remove the organic layer. The aqueous layer was adjusted to pH 3 with 20% aqueous sulfuric acid solution. The solution containing the precipitated product was thoroughly stirred for one hour under ice-cooling. The resulting product was filtered, washed with water and then dried to obtain 50.7 g (Yield 91.5%) of the title compound.

HPLC Purity: 99.3[{]jf44a

EXAMPLE 8

Synthesis of 7-[[2-(2-amino-4-thiazolyl)-2-(Z)-methoxyimino]acetamido]-3-[2,5-dihydro-6-hydroxy-2-methyl-5-oxo-1,2,4-triazin-3-yl)thiomethyl]-3-cephem-4-carboxylic acid (Ceftriaxone)

To 95% ethyl alcohol (400 ml) in a 1 L-round flask were successively added 7-amino-3-[(2,5-dihydro-6-hydroxy-2-methyl-5-oxo-1,2,4-triazin-3-yl)thiomethyl]-3-cephem-4-carboxylic acid (37.1 g), diethylthiophosphoryl-(Z)-(2-aminothiazol-4-yl)methoxyiminoacetate (38.8 g) and triethylamine (30.36 g) with stirring. This reaction solution was stirred for 3 hours while maintaining the temperature at 20° to 25° C. and then concentrated hydrochloric acid (26.04 g) diluted with 95% ethyl alcohol (200 ml) was added thereto. The solution containing the precipitated product was thoroughly stirred for one hour under ice-cooling. The resulting product was filtered, washed with water and then dried to obtain 50.7 g (Yield 91.5%) of the title compound.

HPLC Purity: 99.3[{]jf44a

EXAMPLE 9

Synthesis of 7-[[2-(2-amino-4-thiazolyl)-2-(Z)-methoxyimino]acetamido]-3-[(1-methyl-1H-tetrazol-5-yl)thiomethyl]-3-cephem-4-carb oxylic acid (Cefmenoxime)

To a 1 L-round flask were added distilled water (100 ml), 7-amino-3-[(1-methyl-1H-tetrazol-5-yl)thiomethyl]-3-cephem-4-carboxylic acid (32.8 g) and sodium hydrogen carbonate (16.8 g) and the mixture was allowed to completely dissolve with stirring at room temperature. Then diethylthiophosphoryl-(Z)-(2-aminothiazol-4-yl)methoxyiminoacetate (38.8 g) dissolved in tetrahydrofuran (100 ml) was added thereto and the reaction mixture was stirred at 20° to 25° C. for 5 hours. Ethyl acetate (2×100 ml) was added to the reaction solution to separate the organic layer. Then the aqueous layer was adjusted to pH 3.1 with 2N-aqueous hydrochloric acid solution and stirred for one hour under ice-cooling. The resulting precipitate was filtered, washed with water and then dried to obtain 46.3 g (Yield 90.6%) of the title compound.

HPLC Purity: 99.4[{]jf44a

EXAMPLE 10

Synthesis of 7-[[2-(2-amino-4-thiazolyl)-2-(Z)-methoxyimino]acetamido-3-[(1-methyl-1H-tetrazol-5-yl)thiomethyl]-3-cephem-4-carboxylic acid Cefmenoxime)

To 95% ethyl alcohol (400 ml) in a 1 L-round flask were successively added 7-amino-3-[(1-methyl-1H-tetrazol-5-yl)thiomethyl]-3-cephem-4-carboxylic acid (32.8 g), diethylthiophosphoryl-(Z)-2-(2-aminothiazol-4-yl)methoxyiminoacetate (38.8 g) and triethylamine (20.24 g) with stirring. The reaction mixture was then stirred at 20° to 25° C. for 5 hours and concentrated hydrochloric acid (15.63 g) diluted with 95% ethyl alcohol (200 ml) was added thereto. The reaction mixture was stirred for one hour under ice-cooling. The resulting precipitate was filtered, washed with water and then dried to obtain 46.3 g (Yield 90.6%) of the title compound.

HPLC Purity: 99.4[{]jf44a

EXAMPLE 11

Synthesis of 7-[[2-methoxyimino-2-(2-amino-1,3-thiazol-4-yl)]acetamido]-3-cephem-4-carboxylic acid (Ceftizoxime)

To a-1 L-round flask were added distilled water (100 ml), 7-amino-3-cephem-4-carboxylic acid (20 g) and sodium hydrogen carbonate (16.8 g) and the mixture was allowed to completely dissolve with stirring at room temperature. Then diethylthiophosphoryl-(Z)-2-(2-aminothiazol-4-yl)methoxyiminoacetate (38.8 g) dissolved in tetrahydrofuran (100 ml) was added thereto and the reaction mixture was stirred at 20° to 25° C. for 5 hours. Ethyl acetate (2×100 ml) was added to the reaction solution to separate the organic layer. Then the aqueous layer was adjusted to pH 3 with 2N-aqueous hydrochloric acid solution and stirred for one hour under ice-cooling. The resulting precipitate was filtered, washed with water and then dried to obtain 35.8 g (Yield 93.4%) of the title compound.

HPLC Purity: 98.4[{]jf44a

EXAMPLE 12

Synthesis of 7-[[2-methoxyimino-2-(2-amino-1,3-thiazol-4-yl)]acetamido]-3-cephem-4-carboxylic acid (Ceftizoxime)

To 95% ethyl alcohol (400 ml) in a 1 L-round flask were successively added 7-amino-3-cephem-4-carboxylic acid (20 g), diethylthiophosphoryl-(Z)-2-(2-aminothiazol-4-yl)methoxyiminoacetate (38.8 g) and triethylamine (20.24 g) with stirring. The reaction mixture was-then stirred at 20° to 25° C. for 5 hours and concentrated hydrochloric acid (15.63 g) diluted with 95% ethyl alcohol (200 ml) was added thereto. The reaction mixture was stirred for one hour under ice-cooling. The resulting precipitate was filtered, washed with water and then dried to obtain 35.8 g (Yield 93.4%) of the title compound.

HPLC Purity: 98.4%

EXAMPLE 13

Synthesis of 7-[[2-(2-amino-4-thiazolyl)-2-(Z)-methoxyimino]acetamido]-3-(2,3-cyclopentenopyridiniummethyl)-3-cephem-4-carboxylate (Cefpirome) sulfate To distilled water (100 ml) and tetrahydrofuran (100 ml) in a 1 L-round flask were successively added 7-amino-3-(2,3-cyclopentenopyridiniummethyl)-3-cephem-4-carboxylic acid (45.9 g), diethylthiophosphoryl-(Z)-(2-aminothiazol-4-yl)methoxyiminoacetate (38.8 g) and tri-n-butylamine (37.2 g) with stirring. This reaction solution was stirred for 3 hours while maintaining the temperature of 20° to 25° C. and then ethyl acetate (2×100 ml) was added thereto to remove the organic layer. The aqueous layer was adjusted to pH 1.2 with 20% aqueous sulfuric acid solution. To this solution was slowly added ethyl alcohol (300 ml) while maintaining the temperature of 0° to 5° C. and then the mixture was stirred for one hour. The resulting precipitate was filtered, washed with water and then dried to obtain 47.1 g (Yield 76.9%) of the title compound.

HPLC Purity: 98.1[{]jf44a

EXAMPLE 14

Synthesis of 7-[[2-(2-amino-4-thiazoly)-2-(Z)-methoxyimino]acetamido]-3-(2,3-cyclopentenopyridiniummethyl)-3-cephem-4-carboxylate (Cefpirome) sulfate To 95% ethyl alcohol (400 ml) in a 1 L-round flask were successively added 7-amino-3-(2,3-cyclopentenopyridiniummethyl)-3-cephem-4-carboxylic acid (45.9 g), diethylthiophosphoryl-(Z)-(2-aminothiazol-4-yl)methoxyiminoacetate (38.8 g) and triethylamine (20.2 g) with stirring. This reaction solution was stirred for 3 hours while maintaining the temperature of 20° to 25° C. and then concentrated sulfuric acid (12.25 g) diluted with 95% ethyl alcohol (300 ml) was added thereto. The mixture was stirred for one hour while maintaining the temperature of 0° to 5° C. The resulting precipitate was filtered, washed with water and then dried to obtain 47.1 g (Yield 76.9%) of the title compound.

HPLC Purity: 98.1[{]jf44a

EXAMPLE 15

Synthesis of 7-[[2-(2-amino-4-thiazolyl)-2-methoxyimino]acetamido]-3-(1-methylpyrrolidiummethyl)-3-cephem-carboxylate (Cefepime) sulfate To distilled water (100 ml) and tetrahydrofuran (100 ml) in a 1 L-round flask were successively added 7-amino-3-(1-methylpyrrolidiummethyl) -3-cephem-4-carboxylate hydroiodide salt (43.4 g), diethylthiophosphoryl-(Z)-(2-aminothiazol-4-yl)methoxyiminoacetate (38.8 g) and triethylamine (20.2 g) with stirring. This reaction solution was stirred for 4 hours while maintaining the temperature of 20° to 25° C. and then ethyl acetate (2×100 ml) was added thereto to remove the organic layer. To the aqueous layer was added active carbon (5 g) and the mixture was stirred for 30 minutes add then filtered. The filtrate was adjusted to pH 1.2 with 20% aqueous sulfuric acid solution and then acetone (400 ml) was slowly added thereto. The mixture was stirred for one hour. The resulting precipitate was filtered, washed with water and then dried to obtain 45.1 g (Yield 78%) of the title compound.

HPLC Purity: 97.1[{]jf44a

EXAMPLE 16

Synthesis of 7-[[2-(2-amino-4-thiazolyl)-2-methoxyimino]acetamido]-3-(1-methylpyrrolidiummethyl)-3-cephem-4-carboxylate (Cefepime) sulfate To 95% ethyl alcohol (400 ml) in a 1 L-round flask were successively added 7-amino-3-(1-methylpyrrolidiummethyl)-3-cephem-4-carboxylate hydroiodide salt (43.4 g), diethylthiophosphoryl-(Z) -(2-aminothiazol-4-yl)methoxyiminoacetate (38.8 g) and triethylamine (20.2 g) with stirring. This reaction solution was stirred for 4 hours while maintaining the temperature at 20° to 25° C. and then active carbon (5 g) was added thereto. Then, the mixture was stirred for 30 minutes and then filtered. To the filtrate was added concentrated sulfuric acid (12.25 g) diluted with 95% ethyl alcohol (400 ml) and the mixture was stirred for one hour while maintaining the temperature of 0° to 5° C. The resulting precipitate was filtered, washed with water and then dried to obtain 45.1 g (Yield 78%) of the title compound.

HPLC Purity: 97.1%

Although this invention has been described in its preferred form with a certain degree of particularity, it is appreciated by those skilled in the art that the present disclosure of the preferred form has been made only by way of example and that numerous changes in the details of the invention may be resorted to without departing from its spirit and scope.

What is claimed is:

1. A process for preparing cephem derivatives of the following formula (I):

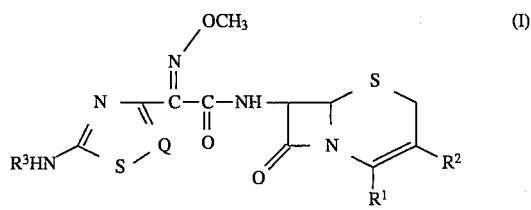

comprising reacting a thiophosphate derivative of thia(dia)zole acetic acid having the following formula (II):

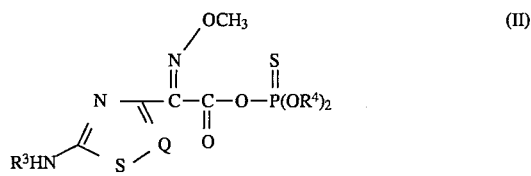

with a 7-ACA derivative having the following formula (III):

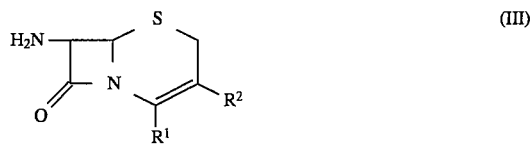

in the presence of a solvent and a base, wherein $R^1$ represents a carboxy group, a protected carboxy group which can form the salt of $—COO^-M^+$ with an alkali metal ion or $—COO^-$ when $R^2$ is selected from the group consisting of pyridinium, pyrimidinium and thiazolium, $R^2$ represents hydrogen, an acetoxymethyl group or a heterocyclic group, wherein said heterocyclic group comprises a saturated or an unsaturated 5 to 6 member monocycle having at least one nitrogen atom in the ring and wherein said heterocyclic group is connected to the 7-ACA moiety through a methyl or thiomethyl group, $R^3$ represents hydrogen or an amino-protecting group, $R^4$ represents $C_1$–$C_4$ alkyl or phenyl, or together with the oxygen or phosphorus atom to which it is attached forms a 5- or 6-membered heterocyclic ring, and represents N or CH.

2. The process according to claim 1, characterized in that the solvent is one selected from dichloromethane, dichloroethane, chloroform, carbon tetrachloride, toluene, xylene, acetonitrile, ethyl acetate, dioxane, tetrahydrofuran, acetone, N,N-dimethylformamide, N,N-dimethylacetamide, alcohols and water, or a mixture of two or more solvents selected therefrom.

3. The process according to claim 2, characterized in that the solvent is water.

4. The process according to claim 3, characterized in that the solvent is an alcohol solvent or an alcohol-water mixed solvent.

5. The process according to claim 4, characterized in that the alcohol is methyl alcohol, ethyl alcohol or isopropyl alcohol.

6. The process according to claim 1, characterized in that the base is selected from carbonates and bicarbonates of an alkali earth metal and tertiary amines.

7. The process according to claim 6, characterized in that the base is sodium hydrogen carbonate, triethylamine or tri-n-butylamine.

8. The process according to claim 6, characterized in that the base is used in an amount of 1.5 to 3.5 equivalent weight with respect to the compound of formula (III).

9. The process according to claim 8, characterized in that the base is used in an amount of 2.0 to 3.0 equivalent weight with respect to the compound of formula (III).

10. The process according to any one of claims 1 to 9, characterized in that the reaction temperature is 0° to 30° C.

11. The process according to claim 10, characterized in that the reaction temperature is 20° to 25° C.

12. The process according to any one of claims 1 to 9, characterized in that the reactive derivative of formula (II) is used in an amount of 1.0 to 1.2 equivalent weight with respect to the compound of formula (III).

* * * * *